United States Patent
Bindernagel et al.

(10) Patent No.: US 10,081,652 B2
(45) Date of Patent: Sep. 25, 2018

(54) PURIFICATION OF EPIDAUNORUBICIN

(71) Applicant: medac Gesellschaft für klinische Spezialpräparate mbH, Wedel (DE)

(72) Inventors: Holger Bindernagel, Gelnhausen (DE); Tero Kunnari, Aschaffenburg (DE)

(73) Assignee: medac Gesellschaft für klinische Spezialpräparate mbH, Wedel (DE)

( * ) Notice: Subject to any disclaimer, the term of this patent is extended or adjusted under 35 U.S.C. 154(b) by 10 days.

(21) Appl. No.: 15/307,488

(22) PCT Filed: Apr. 30, 2015

(86) PCT No.: PCT/EP2015/059441
§ 371 (c)(1),
(2) Date: Oct. 28, 2016

(87) PCT Pub. No.: WO2015/166016
PCT Pub. Date: Nov. 5, 2015

(65) Prior Publication Data
US 2017/0051001 A1   Feb. 23, 2017

(30) Foreign Application Priority Data
Apr. 30, 2014   (DE) .......................... 10 2014 208 194

(51) Int. Cl.
*C07H 15/252* (2006.01)
*C07H 1/06* (2006.01)
*C07H 15/24* (2006.01)

(52) U.S. Cl.
CPC ............. *C07H 15/252* (2013.01); *C07H 1/06* (2013.01); *C07H 15/24* (2013.01)

(58) Field of Classification Search
None
See application file for complete search history.

(56) References Cited

U.S. PATENT DOCUMENTS 4,345,068 A   8/1982   Suarato et al.

FOREIGN PATENT DOCUMENTS

| EP | 0030295 A1 | 11/1980 |
|----|------------|---------|
| EP | 1990405 A1 | 11/2008 |
| EP | 2042608 B1 | 2/2010 |
| EP | 2301943 A1 | 3/2011 |
| WO | 2010028667 A1 | 3/2010 |

OTHER PUBLICATIONS

Bachur, Br. J. Pharmac. (1971), 43, 828-833.*
International Written Opinion dated Aug. 13, 2015 in International Application No. PCT/EP2015/059441 (English translation).
Office Action dated Oct. 27, 2014 in DE Application No. 1020142081947.
Li et al, "Study on the separation and purification of 4'-epi-daunorubicin produced by gene engineering strain SIPI-A0707," Chinese Journal of Antibiotics, vol. 36, No. 11, pp. 839-843, 2011.
International Search Report (with English translation) and Written Opinion dated Aug. 13, 2015 in International Application No. PCT/EP2015/059441.

* cited by examiner

*Primary Examiner* — Layla D Berry
(74) *Attorney, Agent, or Firm* — Panitch Schwarze Belisario & Nadel LLP

(57) ABSTRACT

A method for purifying epidaunorubicin is provided. The purification method involves the removal of the impurity epi-feudomycin, which is formed as a by-product in the biotechnological production of epidaunorubicin.

12 Claims, No Drawings

PURIFICATION OF EPIDAUNORUBICIN

CROSS-REFERENCE TO RELATED APPLICATIONS

This application is a Section 371 of International Application No. PCT/EP2015/059441, filed Apr. 30, 2015, which was published in the German language on Nov. 5, 2015, under International Publication No. WO 2015/166016 A1 and the disclosure of which is incorporated herein by reference.

BACKGROUND OF THE INVENTION

The present invention relates to a method for purifying epidaunorubicin, in particular to the separation of epidaunorubicin and epi-feudomycin, which is formed as a by-product in the biotechnological production of epidaunorubicin.

Epidaunorubicin is a 4'-epimer of daunorubicin, which is in the group of glycosides and represents an antibiotic of the group anthracyclines. It is mainly used as a precursor to epirubicin which is used as a cytostatic in chemotherapy of breast cancer, non-Hodgkin lymphoma, sarcoma, stomach carcinoma and other solid types of cancer. Epidaunorubicin can be produced synthetically, semi-synthetically and biotechnologically. In the biotechnological production, various *Streptomyces peucetius* strains are used. Epidaunorubicin can be represented by the following general formula (I):

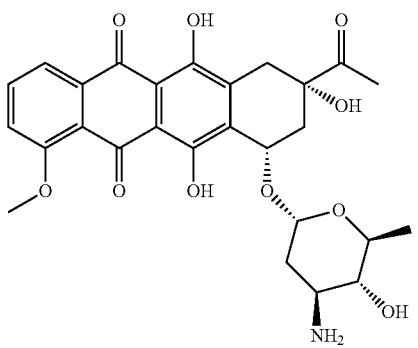

In the microbial synthesis of the epidaunorubicin, the problem arises that in addition to the desired product, epi-feudomycin, inter alia, is formed as a by-product which, due to its structural similarity, is very hard to separate from the epidaunorubicin. The presence of the by-product is detrimental to the yield and degree of purity of the epirubicin which is formed from the epidaunorubicin in a subsequent process step. Usually, the separation and purification of the epidaunorubicin from the fermentation broth is carried out by means of liquid-liquid extraction, chromatography and crystallization.

However, due to the presence of the epi-feudomycin, this requires a complicated process and results in a relatively high loss of epidaunorubicin.

EP 1 990 405 A1 describes different microbial strains which are suitable for the biotechnological production of epidaunorubicin. The separation of the epidaunorubicin from the fermentation broth is carried out via extraction with chloroform at an alkaline pH value. The resulting raw mixture is then further purified chromatographically with chloroform as the mobile phase. In a last step, the epidaunorubicin is crystallized by the addition of butanol and the adjustment of an acidic pH value.

EP 2 301 943 B1 describes the crystallization of epidaunorubicin hydrochloride from a mixture of alcohol/chloroform, whereby the alcohol is added at a temperature of 60° C.

EP 0 030 295 B1 discloses the synthetic production of epidaunorubicin.

WO 2010/028667 describes the extraction of 13-DHED, epidaunorubicin and epi-feudomycin from a fermentation broth with the aid of an adsorbing resin.

EP 2 042 608 B1 describes the extraction of aglycones from a fermentation broth containing 13-DHED, epidaunorubicin and feudomycin. The glycosides are extracted from the aqueous phase by means of chloroform at a slightly alkaline pH value. The pH value is kept stable by means of a saturated $NaHCO_3$ solution.

The common methods for purifying epidaunorubicin from a fermentation broth are associated with high technical and financial expenses. The separation of epidaunorubicin and epi-feudomycin, in particular, is especially difficult due to the structural similarity of the two compounds so that an acceptable degree of purity of the epidaunorubicin can only be achieved in conjunction with a considerable yield loss. Due to the difficult separation of the epi-feudomycin, this impurity can also be found in the products derived from the epidaunorubicin, which is particularly disruptive for the conversion to epirubicin. On the other hand, a high degree of purity and a high yield are especially crucial for the subsequent conversion from epidaunorubicin to epirubicin.

Therefore, there is a need for a process which allows for an effective separation of the by-product epi-feudomycin from the desired product epidaunorubicin, without significantly lowering the yield of epidaunorubicin due to the separation and purification steps.

BRIEF SUMMARY OF THE INVENTION

It is therefore an objective of the present invention to provide a method which allows for an effective separation of epidaunorubicin and epi-feudomycin after the microbial production, wherein the yield of purified epidaunorubicin is higher than that obtained with common methods known from the prior art.

DETAILED DESCRIPTION OF THE INVENTION

An objective of the present invention is a method for purifying epidaunorubicin comprising the following steps:
   a) providing a mixture comprising epidaunorubicin, epi-feudomycin and at least one halogen-containing solvent;
   b) adjusting the pH value of the mixture to a range of 5.0 to 7.5;
   c) heating the mixture of step b) to more than 25° C.; and
   d) purifying the epidaunorubicin.

The content of alcohols with 1 to 5 carbon atoms in the mixture of steps a) and b) does not exceed 5 vol.-%, based on the total volume of the mixture.

Without being bound by theory, it is assumed that under the conditions of the method according to the present invention, the epi-feudomycin is selectively disintegrated and the resulting degradation products are easier to separate from the desired epidaunorubicin. It is assumed that the method according to the present invention also leads to a conversion of the reaction mixture and, accordingly, to a reduction in the epi-feudomycin. Mass spectrometric analyses suggest that the sugar is split off and the remaining ring is aromatized. It is furthermore assumed that this is a specific disintegration of the epi-feudomycin, since no degradation products of epidaunorubicin could be detected. In this respect, the disintegration in the method according to the present invention differs from the conventional acidic hydrolysis of the anthracyclines which would also apply to epidaunorubicin.

The method according to the present invention starts with epidaunorubicin as a raw material which is purified in several steps. The origin and method of production of the epidaunorubicin are not limited in any way. For instance, commercially available epidaunorubicin can be used which contains a portion of epi-feudomycin, which makes it unsuitable for other applications.

In a preferred embodiment of the purification method according to the present invention, the epidaunorubicin of the mixture of step a) is obtained by means of biotechnological methods, for example suitable microorganisms. Preferably, the epidaunorubicin is present in the fermentation broth together with epi-feudomycin. Suitable microorganisms include, for example, bacteria of the group of actinobacteria, in particular strains of the group of Streptomyces sp., for example S. peucetius, S. coeruloruidus, S. griseus, Streptomyces sp. C5, S. peicetius var. caesius and S. bifurcus. Modified strains or mutants can be used as well.

Preferably, the epidaunorubicin and the epi-feudomycin of the mixture of step a) of the method according to the present invention are obtained by means of extraction from the fermentation broth. This extraction can comprise several steps, for example, the extraction by means of a suitable polymer resin followed by a liquid extraction. The mixture a) is preferably obtained from the concentrate of the liquid extraction of the fermentation broth and optionally by adding the halogen-containing solvent.

In an especially preferred embodiment, the starting mixture in step a) has an alkaline pH value. An especially preferred pH value is in the range of 8 to 10.5.

In the mixture a), the epidaunorubicin is present in dissolved form in the presence of at least one halogen-containing solvent. In a preferred embodiment, the halogen-containing solvent is selected from the group of chlorinated solvents, in particular chloroform ($CHCl_3$).

The content of alcohols with 1 to 5 carbon atoms in the mixture of steps a) and b) of the method according to the present invention is at most 5 vol.-%, based on the total volume of the mixture.

It has surprisingly been found that a higher content of alcohols with 1 to 5 carbon atoms leads to a reduced reaction rate, which in turn negatively affects the degree of purity of the epidaunorubicin.

Therefore, an embodiment of the present invention is preferred wherein the content of alcohols with 1 to 5 carbon atoms in the mixture of steps a) and b) is at most 4 vol.-%, more preferably 0.1 to 4 vol.-%, most preferably 1.0 to 3 vol.-%, always based on the total volume of the mixture. An alcohol content in this inventive range ensures that the epidaunorubicin remains completely dissolved and that the reaction takes place in a satisfactory time frame.

In one embodiment of the present invention, the alcohol with 1 to 5 carbon atoms is preferably selected from the group consisting of methanol, butanol, propanol, ethanol, isopropanol, pentanol, 2-pentanol, 3-pentanol, 2,2-dimethyipropanol and isobutanol. In an especially preferred embodiment, the alcohol with 1 to 5 carbon atoms is methanol.

Furthermore, in one embodiment, the content of water in the mixture of step a) is preferably at most 1 vol.-%, based on the total volume of the mixture.

It was furthermore surprisingly found that the epidaunorubicin obtained by means of the method according to the present invention has a particularly high degree of purity if the concentration of the epidaunorubicin in the mixture of step a) is no more than 13 g/L.

Therefore, in one embodiment, the concentration of the epidaunorubicin in the mixture of step a) is preferably no more than 13 g/L, more preferably 6 to 13 g/L, and most preferably 8 to 13 g/L. It was found that undesired side reactions and disruptions of the reaction can be prevented if the concentration of the epidaunorubicin in the mixture of step a) is in this range. For instance, the danger of a precipitation of the epidaunorubicin could be reduced. Precipitation of the epidaunorubicin leads to an undesired yield loss, since the precipitated epidaunorubicin is removed from the purification process. Moreover, it was observed that together with the epidaunorubicin, the impurity to be separated, epi-feudomycin, precipitates as well so that precipitation is not a suitable purification method.

According to step b) of the method of the present invention for the purification of epidaunorubicin, the pH value of the mixture is adjusted to a range of 5.0 to 7.5. Surprisingly, it was found that the epidaunorubicin disintegrates if the pH value is above the inventive range. If the pH value is too acidic, i.e. adjusted to a value below 5, an undesired partial protonation of the epidaunorubicin occurs which leads to a precipitation of the epidaunorubicin together with the feudomycin so that it is removed from the subsequent process flow.

Preferably, the pH value of the mixture is adjusted to a range of 5.0 to 7.5 by means of an acid exhibiting both a suitable pKa value and good solubility in the halogen-containing solvent, in particular chloroform. In a preferred embodiment of the method according to the present invention, the pH value of the mixture in step b) is adjusted by means of one or more acids, preferably an organic acid, and more preferably acetic acid.

In another preferred embodiment of the inventive method, the amount of acid is 0.05 to 0.3 vol.-%, preferably 0.1 to 0.25 vol.-%, based on the total volume of the mixture. After addition of the acid, a clear increase in the reaction rate could be observed. On the other hand, if the acid content is more than 0.3 vol.-%, based on the total volume of the mixture, solubility problems can arise which lead to a precipitation of the epidaunorubicin together with the epi-feudomycin from the solution so that they are removed from the subsequent process flow.

In a particularly preferred embodiment, the acid which is used to adjust the pH value in the mixture is dissolved in an alcohol with 1 to 5 carbon atoms, preferably methanol, prior to its addition. As has surprisingly been found, doing so can prevent problems regarding the solubility of the epidaunorubicin and avert precipitation of the epidaunorubicin. The total content of alcohol with 1 to 5 carbon atoms, in particular methanol, in the mixture should not exceed the inventive value of vol.-%, based on the total volume of the mixture.

According to step c) of the inventive method for purifying epidaunorubicin, after the pH value has been adjusted to the inventive range, the mixture of step b) is heated to a temperature above 25° C. It was surprisingly found that the purification can be accelerated if the mixture is heated to a temperature above 25° C. Preferably, the mixture is heated to a temperature which corresponds to the boiling point of the halogen-containing solvent. Temperatures above 50° C. were shown to be especially suitable since, at such temperatures, a significant increase in the reaction rate could be observed.

Therefore, in one embodiment, the mixture of step c) is heated to a temperature in the range of 55° C. to 75° C., preferably 60° C. to 65° C.

In a preferred embodiment, the mixture of the inventive method is stirred for a certain time period at a temperature of more than 25° C., preferably at a temperature of more than 35° C., especially in a range of 60° C. to 65° C. The time period should be of a length which allows for the inventive method to be carried out in an efficient and timely fashion and, at the same time, results in a satisfactory degree of purity of the epidaunorubicin.

Consequently, in one embodiment of the inventive method, the mixture of step c) is stirred for a time period of at most 48 hours, preferably a time period of 10 to 30 hours, and more preferably a time period of 15 to 25 hours. A reaction time of more than 48 hours was found to be disadvantageous from a procedural point of view, while after a reaction time of less than 10 hours, the decrease in the epi-feudomycin content of the mixture was found to be insufficient. In one embodiment, the mixture in step c) is stirred until the total content of epi-feudomycin is less than 1 wt.-%, based on the total weight of the epidaunorubicin, as long as the reaction time of 48 hours is not exceeded. The amount of epi-feudomycin in the mixture can be, for example, determined by means of standardized chromatography processes such as RP-18 HPLC.

As is described in step d) of the method according to the present invention, the epidaunorubicin is purified. This purification is preferably carried out at a time when the total content of epi-feudomycin has dropped below a threshold of 1 wt.-%, based on the weight of the epidaunorubicin, determined by means of analytical chromatography. It is furthermore preferred that the purification of the epidaunorubicin in step d) is carried out by means of aqueous extraction.

During the purification of the epidaunorubicin in step d), it was found to be advantageous if the aqueous extraction of the epidaunorubicin in step d) is carried out in an alkaline medium. Therefore, in a preferred embodiment, the aqueous extraction of the epidaunorubicin in step d) of the inventive method is carried out at a pH value of 8 to 10, preferably 8.5 to 9.5. The pH value can be adjusted, for example, by means of ammonia. It was found to be especially advantageous if the ammonia contains about 0.5 to 1.5 wt.-% NaCl, for example about 1 wt.-% NaCl, in order to prevent a partial transition of the epidaunorubicin from the organic phase to the aqueous phase. The amount of ammonia needed to adjust the desired pH value can vary and depends on the amount of acid added. For example, the amount of ammonia needed can be 2.5 times the amount of acid in grams.

A high degree of purity of the epidaunorubicin is essential for the subsequent conversion of the epidaunorubicin to epirubicin, since this is the only way to increase the yield. Therefore, in a preferred embodiment of the method according to the present invention, step d) is followed by another step e), wherein step e) is a chromatographic purification of the epidaunorubicin. The chromatographic purification is preferably carried out with silica gel ($SiO_2$) as the stationary phase, while a mixture of methanol and chloroform is preferably used as the mobile phase. This has the advantage that the solvent does not have to be changed which, in turn, contributes to the increased efficiency of the method according to the present invention.

It was surprisingly found that the load of the chromatography column with epidaunorubicin purified according to the method of the present invention could be increased, as compared to epidaunorubicin purified with conventional processes, without resulting in a deterioration of the separation performance. This represents yet another advantage of the method according to the present invention, since a higher load of the column in combination with the same separation performance allows for a more efficient and more economical process cycle. Surprisingly, it was found that the load of the chromatography column with epidaunorubicin purified according to the method of the present invention could be increased to up to 7 wt.-%, based on the dry weight of the column matrix, while the maximum load of the column in conventional processes is about 4 wt.-%.

In another preferred embodiment of the method according to the present invention, the epidaunorubicin of step e) is subjected to further purification processes, for example, a crystallization. The crystallization can be carried out, for example, in the form of the hydrochloride salt. In this regard, it was found that the quality of the epidaunorubicin purified according to the method of the present invention is so high after only one crystallization step, that there was no need for the second crystallization step commonly carried out in conventional separation processes of the prior art.

In an especially preferred embodiment of the method according to the present invention, the method comprises the following steps:
a) providing a mixture comprising epidaunorubicin, epi-feudomycin and at least one halogen-containing solvent, preferably chloroform, wherein the content of feudomycin is higher than 1 wt.-%, based on the total weight of epidaunorubicin and epi-feudomycin;
b) adjusting the pH value of the mixture to a range of 5.0 to 7.5;
c) heating the mixture of step b) to a temperature in the range of 55° C. to 75° C., preferably 60° C. to 65° C.;
d) purifying the epidaunorubicin, preferably by means of aqueous extraction; and
e) chromatographic purification of the epidaunorubicin of step d), wherein the content of alcohols with 1 to 5 carbon atoms in the mixture of steps a) and b) is 0.1 to 4 vol.-%, preferably 1.0 to 3.0 vol.-%, based on the total volume of the mixture, and the amount of water in mixture of step a) is at most 1 vol.-%, based on the total volume of the mixture.

In another preferred embodiment, the method according to the present invention comprises the following steps:
a) providing a mixture comprising epidaunorubicin, epi-feudomycin and at least one halogen-containing solvent, preferably chloroform, wherein the content of feudomycin is higher than 1 wt.-%, based on the total weight of epidaunorubicin and epi-feudomycin, and the concentration of the epidaunorubicin is in a range of 6 to 13 g/L;
b) adjusting the pH value of the mixture to a range of 5.0 to 7.5;
c) heating the mixture of step b) to a temperature in the range of 55° C. to 75° C., preferably 60° C. to 65° C.;
d) purifying the epidaunorubicin by means of aqueous extraction, wherein the pH value of the extraction mixture is in the range of 8 to 10, preferably 8.5 to 9.5; and
e) chromatographic purification of the epidaunorubicin of step d), wherein the content of alcohols with 1 to 5 carbon atoms in the mixture of steps a) and b) is 0.1 to 4 vol.-%, preferably 1.0 to 3.0 vol.-%, based on the total volume of the mixture, and the amount of water in mixture of step a) is at most 1 vol.-%, based on the total volume of the mixture.

In a preferred embodiment, the individual process steps a) to e) are not interchangeable. It is especially preferred that the method be carried out in the order as given.

The invention will be explained in more detail in the following Examples. However, the following Examples shall not restrict the inventive concept in any way.

EXAMPLES

Example 1

The concentration of epidaunorubicin in a mixture comprising chloroform ($CHCl_3$), epidaunorubicin and epi-feudomycin was set to a content of 8 to 12 g/L by way of distillation. A corresponding starting mixture can be obtained, for example, by separating the chloroform phase from the fermentation broth. 194 g acetic acid (0.15 vol.-%) and 2.4 kg methanol (2 vol.-%) were added to the concentrated solution (128 L), wherein the amounts given in vol.-% refer to the total volume of the solution, and the pH value was thus adjusted to a range of 5.0 to 7.5. The resulting solution was heated to 60° C. to 65° C. and stirred for 17 hours at that temperature range. Then, the mixture was cooled to 25° C. and the content of the impurity epi-feudomycin, based on the weight of epidaunorubicin, was determined by means of analytical HPLC (RP 18-HPLC) and integration of the measured peaks. The results are shown in Table 1.

Example 2 serves as a Comparative Example and shows the result of a conventional purification of epidaunorubicin, wherein the mixture was not heated to a temperature of 60° C. to 65° C. and no acetic acid was added. The percentages given for epi-feudomycin are based on the amounts of epidaunorubicin.

TABLE 1

| Example | epi-feudomycin (%) |
|---|---|
| 1 | 0.6 |
| 2 (Comparative) | 3.3 |

As can be inferred from Table 1, a higher degree of purity of the epidaunorubicin could be obtained by using the method according to the present invention, which is reflected in the lower content of epi-feudomycin.

In another step, the epidaunorubicin, which has been purified according to the method of the present invention, was further treated by means of aqueous extraction at a pH value of 8 to 9 and subsequent chromatographic purification. Different loads of the column were tested. The fractions obtained during the chromatographic purification were combined, and the degree of purity of the epidaunorubicin and the content of epi-feudomycin were determined. The results are shown in Table 2. The load of the column refers to the weight ratio of epidaunorubicin to the dry weight of the column matrix, multiplied by 100%.

TABLE 2

| Example | Load (%) | Purity (%) | Yield (%) | Content of epi-feudomycin (%) |
|---|---|---|---|---|
| 3 | 5.1 | 91 | 87 | 0.3 |
| 4 | 5.8 | 86 | 97 | 0.2 |
| 5 | 7.2 | 90 | 97 | 0.2 |

As can be inferred from Table 2, even at a high load of the column, the separation performance not only remains unchanged, but could even be increased.

Table 3 shows the results of experiments wherein the amount of acetic acid used for adjusting the pH value was varied. As can be inferred from Table 3, the content of epi-feudomycin decreases as the amount of acid is increased. Chloroform was used as a solvent. The mixtures each contained 1 vol.-% methanol and were stirred for 25 hours at 60° C. before the amount of epi-feudomycin was determined. The amount of epi-feudomycin in the starting mixture was 8.7%. Example 6 is a Comparative Example, wherein no acetic acid was added to the mixture.

TABLE 3

| Example | Acetic acid (vol.-%) | epi-feudomycin (%) |
|---|---|---|
| 6 | 0 | 7.7 |
| 7 | 0.1 | 3.1 |
| 8 | 0.2 | 1.9 |
| 9 | 0.3 | 1.3 |
| 10 | 0.5 | 0.8 |

As is shown in Table 3, even an addition of 0.1 vol.-% of acetic acid to a mixture comprising chloroform, epidaunorubicin, epi-feudomycin and 1 vol.-% methanol leads to a marked decrease in the impurity epi-feudomycin at a reaction time of 25 hours at a temperature of 60° C. Thus, the degree of purity of the resulting epidaunorubicin can be increased without resulting in yield losses due to elaborate purification methods.

As can be inferred from the above Examples, the method according to the present invention leads not only to a significantly higher degree of purity of the epidaunorubicin as compared to conventional purification methods, but also allows for an increase in the efficiency and economy of the purification process due to a higher column load, in combination with at least the same separation performance and reduction of the necessary process steps, such as the dispensability of the second crystallization step.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. Method for purifying epidaunorubicin comprising the following steps:
    a) providing a mixture comprising epidaunorubicin, epi-feudomycin and at least one halogen-containing solvent;
    b) adjusting a pH value of the mixture to a range of 5.0 to 7.5;
    c) heating the mixture of step b) a temperature in the range of 55° C. to 75° C.; and
    d) purifying the epidaunorubicin,
    wherein a content of alcohols with 1 to 5 carbon atoms in the mixture of steps a) and b) is at most 5 vol.-%, based on a total volume of the mixture.

2. Method according to claim 1, wherein a content of water in the mixture of step a) is at most 1 vol.-%, based on the total volume of the mixture.

3. Method according to claim 1, wherein the alcohols with 1 to 5 carbon atoms are selected from the group consisting of methanol, butanol, isopropanol, ethanol, propanol, pentanol, 2-pentanol, 3-pentanol, 2,2-dimethylpropanol and isobutanol.

4. Method according to claim 1, wherein a concentration of the epidaunorubicin in step a) is 6 to 13 g/L.

5. Method according to claim 1, wherein the halogen-containing solvent is selected from the group of chlorinated solvents.

6. Method according to claim 1, wherein in step b), the pH value is adjusted by one or more acids.

7. Method according to claim 6, wherein the amount of the one or more acids is 0.1 to 0.3 vol.-% based on the total volume of the mixture.

8. Method according to claim 1, wherein in step c), the mixture is stirred for a time period of at most 48 hours.

9. Method according to claim 1, wherein the purification of epidaunorubicin in step d) is carried out by aqueous extraction.

10. Method according to claim 9, wherein the aqueous extraction of epidaunorubicin in step d) is carried out at a pH value of 8 to 10.

11. Method according to claim 1, further comprising, after step d), a step e) of a chromatographic purification of epidaunorubicin.

12. Method according to claim 6, wherein in step b), the one or more acids is an organic acid.

* * * * *